US006830750B1

(12) United States Patent
Naruszewicz

(10) Patent No.: US 6,830,750 B1
(45) Date of Patent: Dec. 14, 2004

(54) **REDUCTION OF OXIDATIVE STRESS FACTORS WITH *LACTOBACILLUS PLANTARUM***

(75) Inventor: Marek Naruszewicz, Zalesie Gorne (PL)

(73) Assignee: Probi AB, Lund (SE)

( * ) Notice: Subject to any disclaimer, the term of this patent is extended or adjusted under 35 U.S.C. 154(b) by 0 days.

(21) Appl. No.: 09/787,893

(22) PCT Filed: Oct. 1, 1999

(86) PCT No.: PCT/SE99/01741

§ 371 (c)(1),
(2), (4) Date: May 24, 2001

(87) PCT Pub. No.: WO00/20013

PCT Pub. Date: Apr. 13, 2000

(30) Foreign Application Priority Data

Feb. 4, 1999 (SE) ............................................. 9900371
Oct. 1, 1999 (SE) ............................................. 9803334

(51) Int. Cl.$^7$ ................................................. C12N 1/20
(52) U.S. Cl. ........................... 424/93.45; 435/252.9; 435/252.1; 435/170
(58) Field of Search .................... 424/93.45; 435/252.1, 435/170, 435

(56) References Cited

U.S. PATENT DOCUMENTS

| 4,314,995 | A |   | 2/1982  | Hata et al. |            |
|-----------|---|---|---------|-------------|------------|
| 5,587,314 | A | * | 12/1996 | Bergmark    | 424/93.45  |
| 6,159,465 | A | * | 12/2000 | Adlerberth  | 424/93.45  |
| 6,214,336 | B1|   | 4/2001  | Bukowska et al. |        |
| 6,228,358 | B1| * | 5/2001  | Toba et al. | 424/93.45  |

FOREIGN PATENT DOCUMENTS

| WO | WO 94/26133 |   | 11/1994 |
|----|-------------|---|---------|
| WO | 94/26133    | * | 11/1994 |
| WO | WO 98/00035 |   | 1/1998  |

OTHER PUBLICATIONS

M. T. Nenonen, et al., Br. J. Rheumatol., AN 09478714, vol. 37, No. 3, p. 274–281, "Uncooked, Lactobacilli–Rich, Vegan Food and Rheumatoid Arthritis", Mar. 1998 (Abstract only).

Derwent Abstracts, JP 5–009124, Jan. 19, 1993.

N. Huang, et al., Cytokine, AN 06821350, vol. 9, No. 1, pp. 27–36, "Inhibition of IL–8 Gene Expression in Caco–2 Cells by Compounds Wich Induce Histone Hyperacetylation", 1997 (Abstract only).

K. Yl, Nutr. Rev., AN 09429705, vol. 56 (1 Pt 1), pp. 17–24, "Short–Chain Fatty Acids in Ulcerative Colitis", Jan. 1998 (Abstract only).

U. Siigur, et al., Microbial Ecology in Health and Disease, AN 10971268, vol. 9, No. 6, pp. 271–277, "Effect of Bacterial Infection and Administration of a Probiotic on Faecal Short–Chain Fatty Acids", 1996 (Abstract only).

T. A. Lisitsyna, et al., Vestnik Rossiiskoi Akademii Medtsinskikh Nauk, AN 10835770, vol. 12, pp. 15–20, "Active Forms of Oxygen and Pathogenesis of Rheumatic Arthritis and Systemic Lupus Erythematosus", 1996 (Abstract only).

T. K. Nabukhotnyi, et al., Vopr Pitan, AN 04285102, vol. 6, pp. 27–30, "Use of Adapted Maliutka and Malysh Propionibacterium Acidophilus Mixtures in the Combined Treatment of Acute Diseases of the Gastrointestinal Tracts in Infants", Nov.–Dec. 1983 (Abstract only).

K. Tanaka, et al., Immunopharmacology, AN 07527508, vol. 40, No. 3, pp. 209–217, "The Effects of Nonsteroidal Anti–Inflammatory Drugs on Immune Functions of Human Peripheral Blood Mononuclear Cells", 1998 (Abstract only).

* cited by examiner

*Primary Examiner*—Irene Marx
(74) *Attorney, Agent, or Firm*—Oblon, Spivak, McClelland, Maier & Neustadt, P.C.

(57) ABSTRACT

The invention refers to the use of a bacterial strain, preferably of the genus *Lactobacillus* or *Propionibacterium*, giving rise to increased amounts of propionic acid in the gut for the manufacture of a medicament for reduction of the level of oxidative stress factors, such as IL-6, reactive oxygen species (ROS), and adhesion molecules in mammals including man. The medicament can be used for the prophylaxis and/or treatment of chronic inflammatory diseases such as rheumatic diseases and psoriasis.

12 Claims, 3 Drawing Sheets

REDUCTION OF OXIDATIVE STRESS FACTORS WITH *LACTOBACILLUS PLANTARUM*

The present invention refers to the use of one or more bacterial strains to reduce the level of oxidative stress factors in mammals including man.

BACKGROUND OF THE INVENTION

Oxidative stress factors is the common term for a number of molecules primarily causing prooxidant conditions in the body. Said factors, such as IL-1, IL-6, ROS (reactive oxygen species), IL-8,8-isoprostaglandin, VCAM (vascular cell adhesion molecule) and ICAM (intracellular adhesion molecule) are present at an elevated level in proinflammatory and inflammatory states.

The oxidative stress factors can also be designated inflammatory markers, which expression, however, in addition comprises so called secondary molecules, which are initiated by the oxidative stress factors, for example acute phase proteins.

ROS, as well as the other oxidative stress factors, are produced by the monocytes and lymphocytes. Normal production of the specific level serve to maintain homeostasis in the body.

An elevated level of oxidative stress factors is typical for acute and chronic inflammation. In chronic inflammation there is a risk of an increased ageing process, atherosclerosis and cancer. Chronic inflammatory states are for instance induced by heavy smoking or by chronic infections with viruses and bacteria. Another group of chronic inflammatory diseases comprises autoimmune conditions such as rheumatic diseases and psoriasis.

Chronic inflammation patients are today treated with antibiotics, high doses of vitamins or other drugs. The use of antibiotics should for several reason be avoided and the use of drugs is mostly associated with different unwanted side-effects. Rheumatic diseases are for instance treated with the drug ibuprofen which is effective but expensive and gives gastric side-effects. For psoriasis patients there is no real medication.

PRIOR ART

EP 0 649 603 A1 in the name of Otsuka Pharmaceutical Co., Ltd. refers to an antioxidant food comprising a fermentation product of a food containing a manganese-containing natural material, such as tea leaves, by means of a microbe such as Lactobacillus plantarum. The reason for choosing said bacterium is said to be the catalase activity as well as superoxide dismutase-like activity thereof, which brings about an antioxidant activity in the body, but only in the presence of manganese.

Nenonen, MT., et al., British Journal of Rheumatology, March 1998, 37(3) p 274-81, describes the effect of uncooked lactobacilli-rich vegan food in rheumatoid patients. Half of the patients experienced adverse effects such as nausea and diarrhoea and therefore stopped the experiment, but the other half experienced a subjective release of symptoms. It is speculated that a daily consumption of lactobacilli might have a positive effect also on objective measures of rheumatoid arthritis.

U.S. Pat. No. 4,314,995 in the name of Seikenkai refers to a process for treating a patient having an infection or an inflammation caused by an infectious disease, which comprises administering at least one Lactobacillus which has different nutritional requirements compared to known strains of Lactobacillus, that is which has the ability to grow on a special low nutrition culture medium. Five different strains of Lactobacillus are mentioned as being of the invention.

International Journal of Food Microbiology, 42 (1998) 29–38, discloses a significant increase in the total faecal concentration of the short-chain fatty acids (SCFA) acetic acid and propionic acid after 3 weeks of intake of 400 ml/d of a rose-hip drink containing oats fermented with the probiotic *Lactobacillus plantarum*. This increase, which is said to be independent from the basal diet, can either be explained by a production of SCFA by the administered probiotic strain or by said strain stimulating or suppressing other SCFA producing bacteria in the colon.

DESCRIPTION OF THE INVENTION

The present invention refers to the use of a bacterial strain giving rise to increased amounts of propionic acid in the gut for the manufacture of a medicament for reduction of the level of oxidative stress in mammals including man.

The invention especially refers to the use of a bacterial strain giving rise to increased amounts of propionic acid in the gut for the manufacture of a medicament for reduction of the level of IL-6, ROS, and the adhesion of monocytes to endothelial cells in mammals including man.

A high level of oxidative stress factors, such as the cytokines interleukin 1 and interleukin 6, ROS, and the adhesion of monocytes to endothelial cells is a characteristic of proinflammatory and inflammatory states.

The bacterial strain giving rise to increased amounts of propionic acid in the gut is preferably a strain of *Lactobacillus* or *Propionibacterium*.

According to a preferred embodiment of the invention the bacterial strain is a *Lactobacillus plantarum* strain. A preferred strain of *Lactobacillus plantarum* is the strain *Lactobacillus plantarum* 299v, which has been deposited at the DSM, Deutsche, Sammlunq von Mikroorganismen von Zellkulturen GmbH, Mascheroder Weg1b Braunscheweig, Germany, under the accession number DSM 9843.

The invention also refers to the use of a bacterial strain giving rise to increased amounts of propionic acid in the gut for the manufacture of a medicament for the prophylaxis and/or treatment of chronic inflammatory diseases. Chronic inflammatory or proinflammatory diseases which can be treated according to the invention can be induced by different bacteria, such as *Chlamydia pneumoniae* and *Helicobacter pylori*, or toxic substances, such as nicotine. It has for instance been demonstrated that the number of antibodies against Helicobacter pylori was reduced after one month consumption of Pro Viva, a rose-hip drink containing oats fermented with *Lactobacillus plantarum* DSM 9843 ($5 \times 10^7$ cfu/ml) in an amount of 400 ml/d.

A preferred use according to the invention is for the prophylaxis and/or treatment of autoimmune diseases, such as rheumatic diseases, and psoriasis.

Experimental

Figure 1:
FIG. 1 shows the reduction of the adhesion of monocytes to endothelial cells after treatment with fermented oatmeal gruel.

The purpose of the following experiments was to determine the effect of the administration of a probiotic bacterial strain giving rise to increased concentrations of propionic acid in the gut on the level of oxidative stress factors in blood in subjects having an elevated level of said factors. Each person was given 25 ml/d for either 3 or 6 weeks of a concentrated oatmeal gruel fermented with *Lactobacillus plantarum* DSM 9843 (containing $1 \times 10^9$ cfu/ml).

Methods

Peripheral mononuclear cells (PBMC)

PBMC were isolated from heparinized blood by density-gradient centrifugation. The blood was diluted (1:1) in PBS. 25 ml of diluted blood was immediately layered over 15 ml Ficoll-Paque and centrifuged (1900 rpm, 40 min, 22° C.). The mixed mononuclear cell band was removed by aspiration and washed with PBS. Isolated PBMC was counted and divided into two parts. One part was used to determine intracellular ROS production, second one was used to adhesion assay. The mononuclear cell preparation consists of approximately 30% monocytes and 70 lymphocytes.

Endothelial cell isolation and culture

Human umbilical vein endothelial cells (HUVEC) were obtained from umbilical cords by collagenase digestion, as described by Jaffe, E. A., et al., Culture of human endothelial cells derived from umbilical veins, J. Clin Invest, 1973; 52: 2745–2756. In brief, vein of umbilical cords were perfused with PBS to remove blood cells, filled with 0.1% collagenase (Ia type) and left for 10 min at 37° C. The endothelial cell (EC) suspension was supplemented with PBS, fetal bovine serum, and centrifuged at 1200 rpm for 10 min. EC were cultured in M-199 medium under humidified atmosphere at 5 t $CO_2$ at 37° C. The medium also contained 100 U/ml penicillin, 100 µg/ml streptomycin, 2.5 µg/ml fungizone, 20 mM HEPES, 20% FBS and 50 Ag/ml endothelial cell growth supplement (ECGS). HUVEC were cultured in gelatin-coated 25 cm² flasks. The medium was replaced every 2 days until the cells attained confluence (3–5 days). HUVEC purity was assessed by a "coble-stone" morphology typical for quiescent EC and factor VIII staining. Confluent HUVEC were detached by 0.01% trypsin/EDTA antagonized by FBS.

Test 1. Effect on ROS production

In this study the effect of the administration of a concentrated oatmeal gruel fermented with *Lactobacillus plantarum* DSM 9843 to a group of six healthy volunteers with high levels of reactive oxygen species, ROS, due to heavy smoking, was evaluated. The medium age was 32 years and the body mass index 26.6 kg/M². Each person was given 25 mild for a period of 3 weeks.

Blood was collected from the six individuals. Peripheral blood mononuclear cells (PBMC) were separated by Gradisol L density gradient centrifugation as described above.

The measurement of cell oxidation is based on reactive oxygen species (ROS) mediated conversion of nonfluorescent 2,7-dichlorofluorescein (DCFH), loaded into cells as 2,7-dichloro-fluorescein diacetate, into fluorescent DCF with increased fluorescence emission reflecting enhanced oxidative stress. Freshly isolated PBMC, consisting of approximatively 30% monocytes and 70% lymphocytes, were resuspended in phosphate buffered saline (PBS) followed by incubation with 20 µM 2',7-dichlorofluorescein dichlorofluorescein at 37° C. for 30 min in the dark. The cells were then washed with PBS. The relative fluorescence intensity of the fluorophore 2-,7-dichlorofluorescein, which is formed by peroxide oxidation of its nonfluorescent precursor, was detected with cytofluorimetric assay (FACScan, Becton Dickinson). During flow cytometric analysis monocytes and lymphocytes were gated on the basis of forward scater (FCS) and side scater (SCC). The results are expressed as mean fluorescence intensity in the following Table 1.

TABLE 1

Reactive oxygen species (ROS) production by monocytes and lymphocytes isolated from subjects before and after treatment with *L. plantarum* 299v
Mean Fluorescence Intensity (counts)

| | Monocytes | | Lymphocytes | |
|---|---|---|---|---|
| Individual | Before treatment | After treatment | Before treatment | After treatment |
| 1 | 220 | 120 | 86 | 81 |
| 2 | 254 | 369 | 150 | 134 |
| 3 | 562 | 249 | 217 | 169 |
| 4 | 425 | 201 | 172 | 135 |
| 5 | 343 | 204 | 188 | 129 |
| 6 | 338 | 224 | 133 | 106 |

The above data show that the production of ROS was reduced in individuals except number 2, which is a no-responder.

Test 2. Effect if Ibuprofen on ROS Production, a Comparative study

In order to investigate the mechanisms behind the reduction of ROS by ibuprofen, a propionic acid derivative and a well-known antiinflammatory drug, ibuprofen was administered in an amount of 500 mg/d to the same group of six healthy volunteers as participated in the study described in Test 1 for 3 weeks. Preliminary data indicate that the monocytes and the lymphocytes respond in exactly the same way as to the *Lactobacillus plantarum* 299v in the above study.

Test 3. Effect on Production of ROS

Figure 3:
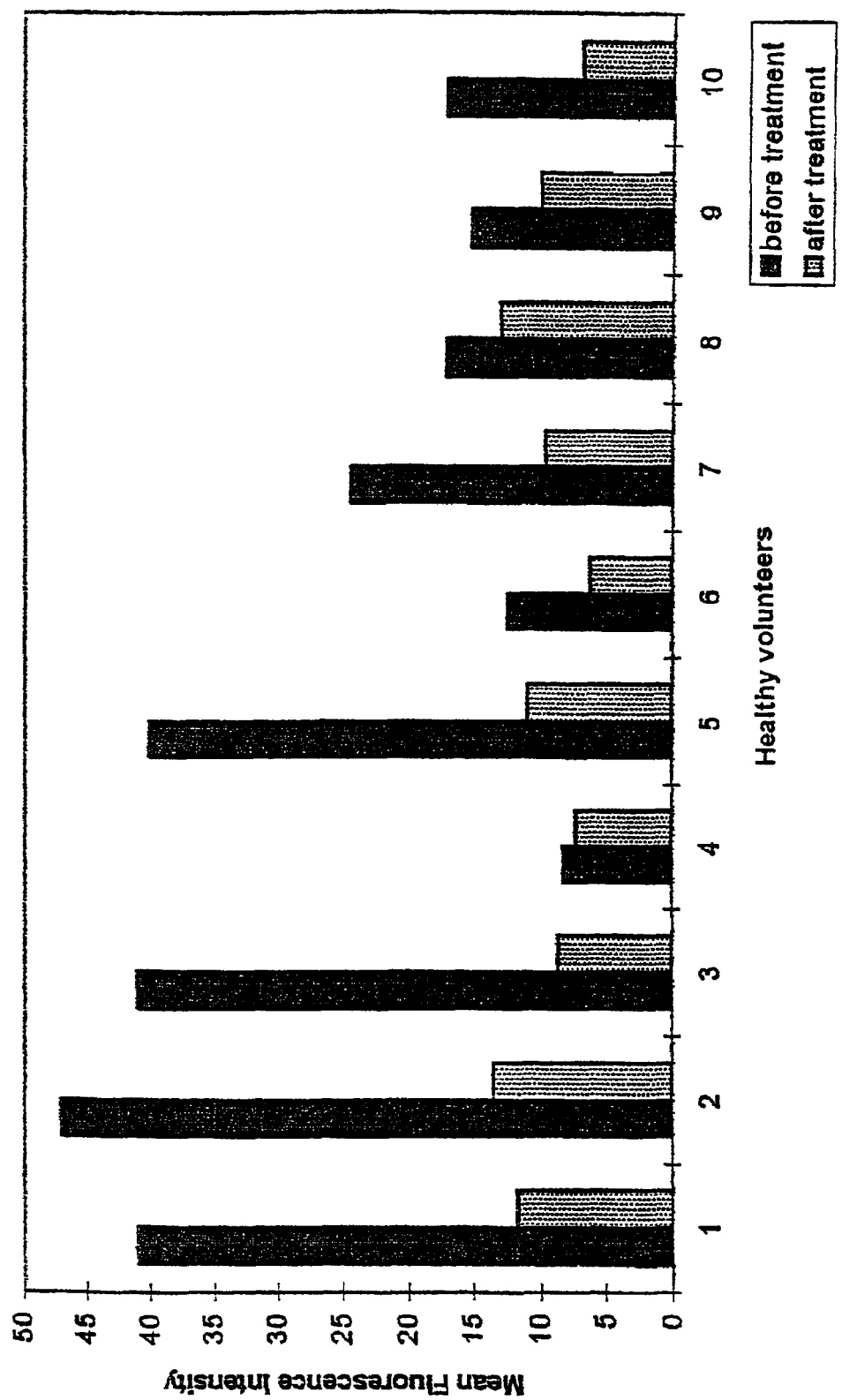
FIG. 3 shows the generation of ROS in monocytes before and after treatment with fermented oatmeal gruel.

The study described in Test 1 was repeated on a group of 10 healthy volunteers (heavy smokers), which were given the concentrated oatmeal gruel for 6 weeks. The results, expressed expressed as mean fluorescence intensity before and after admininstration of the concentrated oatmeal gruel are given in FIG. 3, which illustrates the generation of ROS in normal resting monocytes before and after administration of *Lactobacillus pl.* 299v.

Test 4. Adhesion Assay

PBMC from the same group of 10 healthy volunteers as in Test 3 was also tested as to adhesion in the following way.

For adhesion studies HUVEC of the passage 3 were cultured in gelatin-coated 24-well plates. When confluent monolayers were formed, medium was changed to medium 199 containing antibiotics, 20% FBS and 20 mM HEPES without ECGS 18 hours before experiments. Some cells were pretreated with TNFa (500 u/ml) for 11 hours. Freshly isolated PBMC were resuspended in medium 199 with 20 mM HEPES to a concentration $3–9 \times 10^5$/ml. HUVEC were washed with PBS before addition of PBMC (0,5 ml per well) and coincubated for 30 min. The PBMC suspension was withdrawn. HUVEC were washed with PBS and the wells were fixed with formalin, stained with May-Grunwald and Giemsa solution according to Pappenheim and the number of adherent monocytes were counted in 0.10 separate areas. Data are expressed as percentage of monocyte added. All experiments were performed in duplicate.

Figure 2:
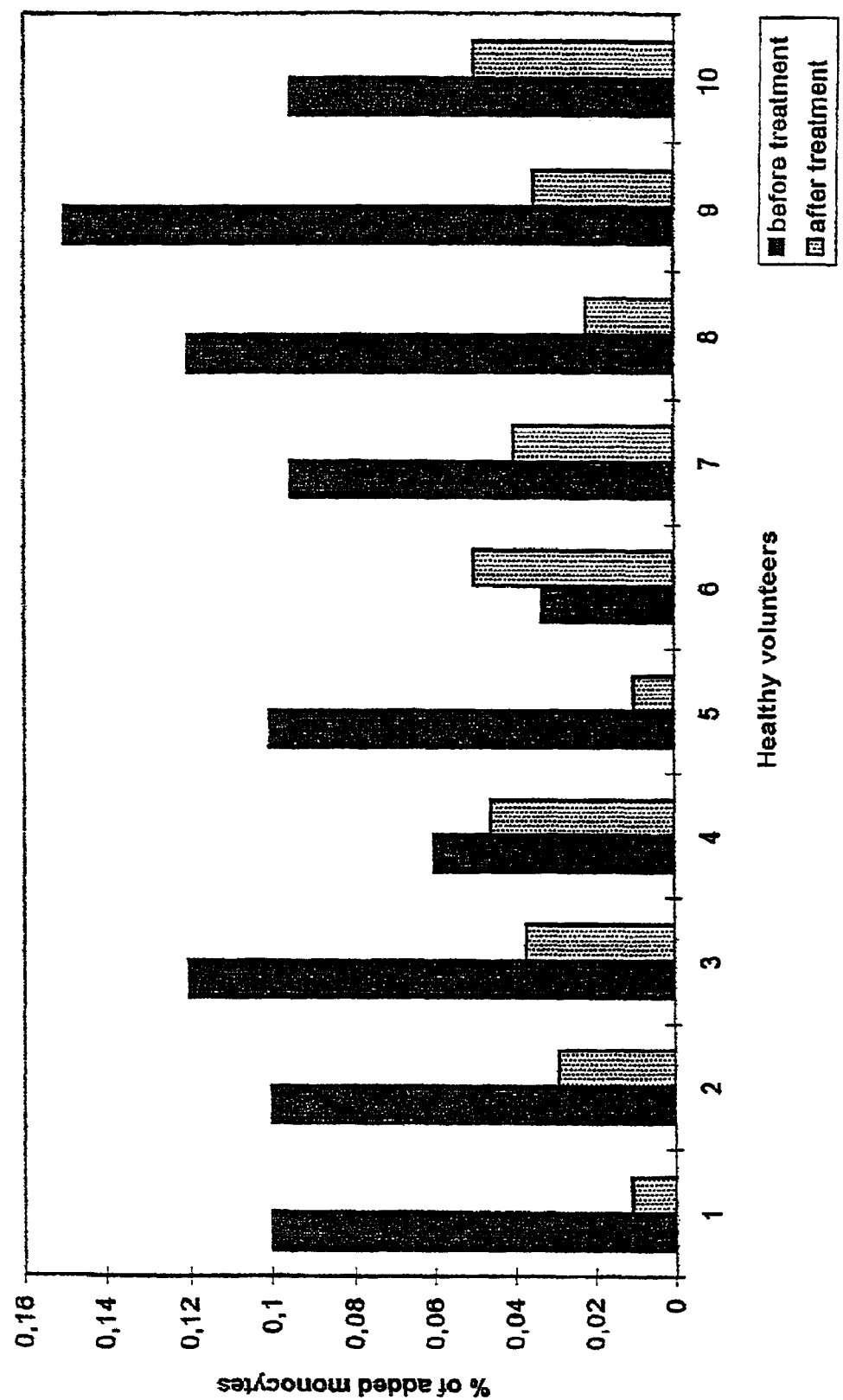
FIG. 2 shows the reduction of the adhesion of monocytes to stimulated endothelial cells after treatment with fermented oatmeal gruel.

The results are given in FIG. 1, illustrating the adhesion of monocytes to non-stimulated HUVEC before and after administration of *Lactobacillus pl.* 299v, and in FIG. 2, illustrating the adhesion of normal resting monocytes to TNF-α-stimulated HUVEC before and after administration of Lactobacillus pl. 299v.

Test 5. Effect on Interleukinf 6 (IL-6)

PBMC from the same group of 10 healthy volunteers as in Test 3 was also tested as to the effect of the concentrated oatmeal gruel on the level of IL-6.

The level of IL-6 was measured by the h-Interleukin-6 ELISA kit from Boehringer Mannheim, which is a photometric enzyme immunoassay for the quantitative in vitro determination of human interleukin-6 (hIL-6) in streptavidin-coated microtiter plates. The results are given in the following Table 2.

TABLE 2

| Subject No. | IL-6 (pg/ml) | IL-6 (pg/ml) |
|---|---|---|
| 1 | 10 | 9 |
| 2 | 11 | 5 |
| 3 | 7 | 11 |
| 4 | 13 | 10 |
| 5 | 14 | 8 |
| 6 | 5 | 5 |
| 7 | 10 | 5 |
| 8 | 7 | 8 |
| 9 | 15 | 9 |
| 10 | 9 | 6 |

Test 6. Propionic Acid Induced Reduction of Oxidative Stress

Human monocyte macrophage cells were isolated as described above and 6 million cells were preincubated in 2 ml of RPMI-1640 medium (10% fetalcalf serum, 50 mg/ml of penicillin/ streptomycin, 2mM glutamine) in dishes having a diameter of 35 mm. 10 μM propionic acid was then added and the cells were incubated at 37° C. for for 4 h. The medium was subsequently removed and replaced with fresh medium and the cells were stimulated with LPS (lipopolysaccharide), 1.0 ng/ml medium, in order to provoke prooxidant stress. After 24 h the medium was removed and concentrated 10 times by evaporation. Oxidative stress with and without (control cells) propionic acid was evaluated using the 8-Isoprostane EIA kit from Cayman Chemical.

The reduction of oxidative stress expressed as the mean value of 3 experiments of the decrease in the 8-isoprostane level was 47%.

Test 7. Reduction of Oxidative Stress Factors in Psoriasis Patients 6 patients with relapsing psoriasis volunteered to participate in the study. The patients were untreated, that is without medication for at least 6 weeks before the start of the administration of the concentrated oatmeal gruel fermented with *Lactobacillus plantarum* DSM 9843 (containing 1×10⁹ cfu/ml). Each patient was given 25 ml/d for 6 weeks.

Peripheral mononuclear cells (PBMC) were isolated from patients before and immediately after the end of the administration of *Lactobacillus*, as described above. The following oxidative stress factors were measured: ROS, before and after stimulation with PMA, phorbol miristate acetate, (100 ng/ml), which stimulates the cells to oxidative stress; adhesion of monocytes to endothelial cells; and IL-6. The results, obtained by the same methods as described above, are given in following Table 3.

TABLE 3

Reduction of oxidative stress factors in psoriasis patients before and after administration of *Lactobacillus pl.* 299v

| Patient No. | | ROS (mfi*) before PMA | ROS (mfi*) after PMA | Adherence (%) | IL-6 (pg/ml) |
|---|---|---|---|---|---|
| 1 | before | 774 | 4209 | 22 | 25 |
|   | after | 781 | 1524 | 13 | 14 |
| 2 | before | 1039 | 5442 | 23 | 18 |
|   | after | 1033 | 3803 | 11 | 9 |
| 3 | before | 660 | 1797 | 26 | 32 |
|   | after | 1175 | 4087 | 11 | 19 |
| 4 | before | 695 | 3772 | — | 29 |
|   | after | 818 | 1516 | — | 17 |
| 5 | before | 840 | 3708 | 30 | 25 |
|   | after | 1348 | 5905 | 20 | 19 |
| 6 | before | 564 | 4019 | 9, 3 | 23 |
|   | after | 1034 | 5520 | 13 | 21 |

*mfi = mean fluorescence intensity

In a clinical evaluation of the patients after 6 weeks treatment 5 of the 6 patients showed a significant decrease in itching. In addition the affected area of the skin had been divided into smaller areas; the decrease in area varied from 10 to 27%.

CONCLUSION

It is suggested that propionate produced in the large gut by colonic microbial fermentation may have an antiinflammatory effect. It is therefore believed that bacterial strains which give rise to increased amounts of propionic acid in the gut will decrease the proinflammatory state connected with different chronic inflammatory disorders in the body.

What is claimed is:

1. A method of reducing a level of at least one oxidative stress factor in the blood of a mammal, comprising administering to a mammal in need thereof *Lactobacillus plantarum* 299v, wherein the level of the at least one oxidative stress factor is reduced compared to the level of the at least one oxidative stress factor in the absence of *Lactobacillus plantarum* 299v and the *Lactobacillus plantarum* 299v is administered to the mammal in need thereof in at least 25 mayday of oatmeal gruel comprising at least 1×10⁹ CFU/mL of *Lactobacillus plantarum* 299v for a time period of from 3 to 6 weeks.

2. The method according to claim 1, wherein the at least one oxidative stress factor is selected from the group consisting of IL-1, IL-6, IL-8,8-isoprostaglandin, vascular cell adhesion molecule, and intracellular adhesion molecule.

3. The method according to claim 1, wherein the at least one oxidative stress is a reactive oxygen species.

4. The method according to claim 1, wherein the at least one oxidative stress factor is produced by at least one member selected from the group consisting of monocytes and lymphocytes.

5. The method according to claim 1, wherein the mammal in need thereof has at least one inflammatory disease or symptoms thereof.

6. The method according to claim 5, wherein the at least one inflammatory disease is selected from the group consisting of atherosclerosis, rheumatic disease, and psoriasis.

7. A method of increasing a level of the fecal concentration of propionic acid in a mammal, comprising administering to a mammal in need thereof *Lactobacillus plantarum* 299v, wherein the level of the fecal concentration of propionic acid is increased compared to the level of the fecal concentration of propionic acid in the absence of *Lactobacillus plantarum* 299v and the *Lactobacillus plantarum* 299v is administered to the mammal in need thereof in at least 25 mL/day of oatmeal gruel comprising at least $1 \times 10^9$ CFU/mL of *Lactobacillus plantarum* 299v for a time period of from 3 to 6 weeks.

8. The method according to claim 7, wherein the mammal in need thereof has at least one inflammatory disease or symptoms thereof.

9. The method according to claim 8, wherein the at least one inflammatory disease is selected from the group consisting of atherosclerosis, rheumatic disease, and psoriasis.

10. A method of reducing a level of adhesion of monocytes to endothelial cells in a mammal, comprising administering to a mammal in need thereof *Lactobacillus plantarum* 299v, wherein the level of adhesion of monocytes to endothelial cells is reduced compared to the level of adhesion of monocytes to endothelial cells in the absence of *Lactobacillus plantarum* 299v and the *Lactobacillus plantarum* 299v is administered to the mammal in need thereof in at least 25 mL/day of oatmeal gruel comprising at least $1 \times 10^9$ CFU/mL of *Lactobacillus plantarum* 299v for a time period of from 3 to 6 weeks.

11. The method according to claim 10, wherein the mammal in need thereof has at least one inflammatory disease or symptoms thereof.

12. The method according to claim 11, wherein the at least one inflammatory disease is selected from the group consisting of atherosclerosis, rheumatic disease, and psoriasis.

* * * * *

UNITED STATES PATENT AND TRADEMARK OFFICE
CERTIFICATE OF CORRECTION

| | | |
|---|---|---|
| PATENT NO. | : 6,830,750 B1 | Page 1 of 1 |
| APPLICATION NO. | : 09/787893 | |
| DATED | : December 14, 2004 | |
| INVENTOR(S) | : Naruszewicz | |

It is certified that error appears in the above-identified patent and that said Letters Patent is hereby corrected as shown below:

On the title page, Item (86), the Filing Date is incorrect. Item (86) should read:

-- (86)  PCT No.: PCT/SE99/01741
   § 371 (c)(1),
     (2), (4) Date: April 26, 2001 --

Also
Item (30) Foreign Application should read:

-- (30) Foreign Application Priority Data

Feb. 4, 1999  (SE) ................................9900371
   Oct. 1, 1998  (SE) ................................9803334 --

Signed and Sealed this

Second Day of October, 2007

JON W. DUDAS
*Director of the United States Patent and Trademark Office*